United States Patent [19]

Fertig et al.

[11] 4,355,234
[45] Oct. 19, 1982

[54] STABLE INFRARED ANALYZER

[75] Inventors: Glenn H. Fertig, Natrona Heights; Daniel R. Nardozzi, Gibsonia; Richard N. Evanuik, Tarentum, all of Pa.

[73] Assignee: Mine Safety Appliances Company, Pittsburgh, Pa.

[21] Appl. No.: 188,982

[22] Filed: Sep. 19, 1980

[51] Int. Cl.³ .......................................... G01N 21/26
[52] U.S. Cl. ................................................. 250/343
[58] Field of Search ................ 250/343, 344, 345, 346

[56] References Cited

U.S. PATENT DOCUMENTS 2,648,775  8/1953  Waters ............................ 250/343 X
3,731,092  5/1973  Freilino .............................. 250/346
4,008,394  2/1977  Risgin et al. ..................... 250/343 X
4,013,260  3/1977  McClatchie et al. ............... 250/343

Primary Examiner—Davis L. Willis

[57] ABSTRACT

A double beam infrared analyzer is modulated to separately and alternately project the sample beam and comparison beam into a condenser microphone type detector thereby generating alternate pulsed signals indicating the intensity of the sample beam and comparison beam. The peak comparison beam signal is detected and maintained at a constant value through a feedback circuit controlling the degree of amplification of both the comparison beam signal and the sample beam signal, thereby providing comparison and sample signals that are corrected every cycle for analyzer instabilities.

7 Claims, 4 Drawing Figures

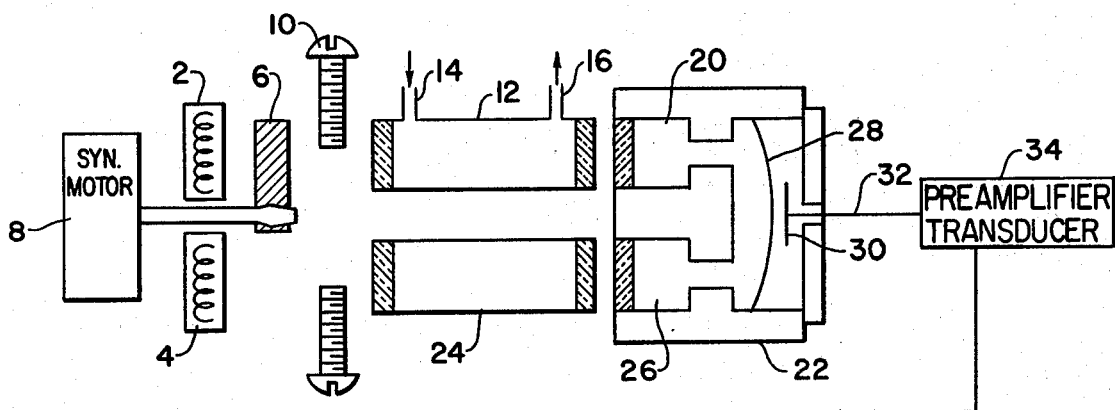
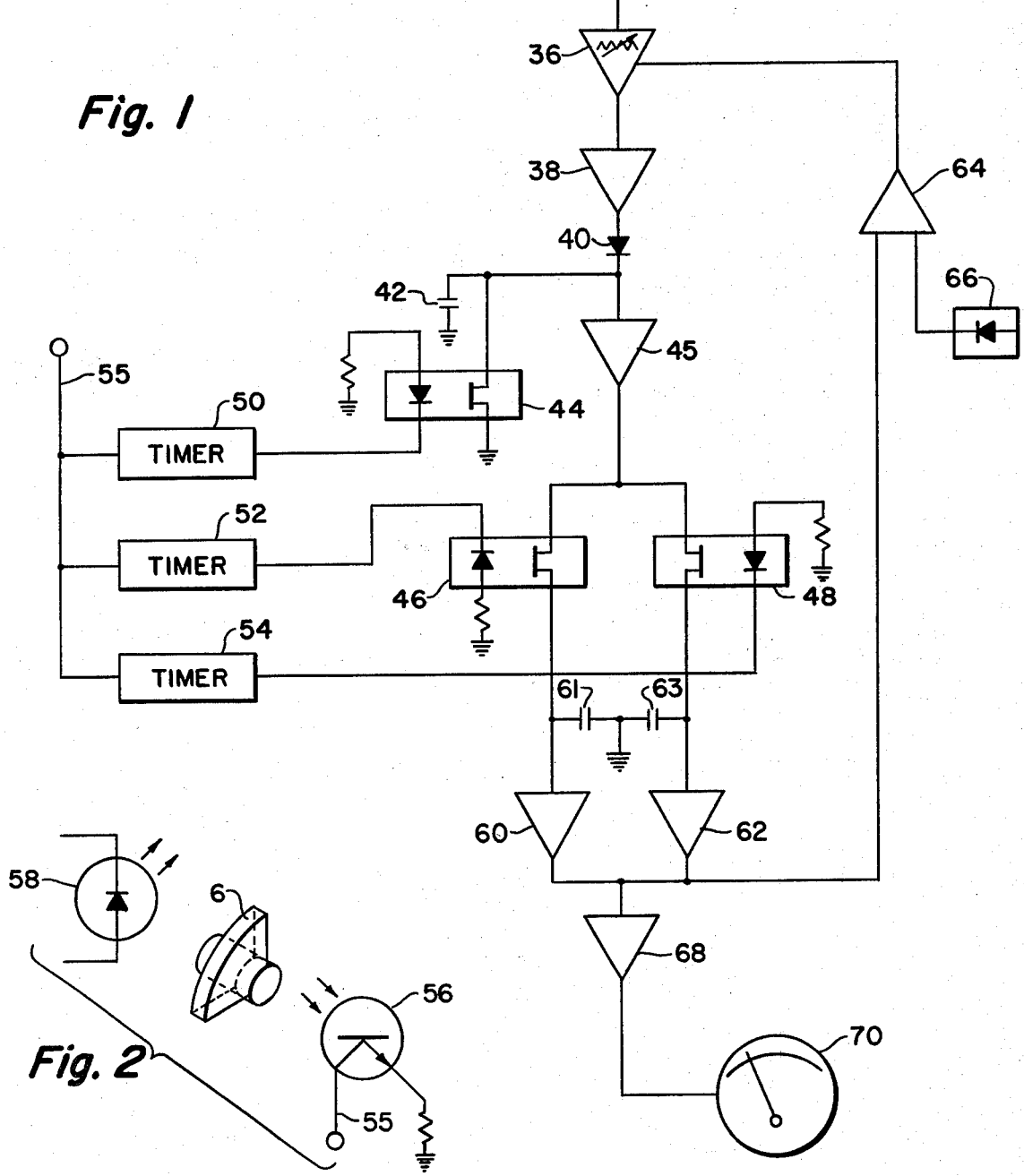
Fig. 1
Fig. 2

STABLE INFRARED ANALYZER

FIELD OF THE INVENTION

This invention relates to double beam infrared fluid analyzers using pneumatic detectors of the condenser microphone type, and more particularly to an improved analyzer having exceptional stability against error resulting from analyzer instabilities. Such errors may result from changes in ambient temperature, changes in the intensity of the infrared energy source, or instabilities in the pneumatic detector or the associated preamplifier and amplifier.

BACKGROUND OF THE INVENTION

In the conventional double beam analyzer with pneumatic detectors, one beam passes through the fluid sample to be analyzed and its attenuated because of absorption of infrared energy in a given spectral range by the presence of the component to be determined; the second beam of substantially equal intensity passes through a comparison fluid, normally substantially nonabsorbent in the measured spectral range of absorbence by the component to be determined. In Waters, U.S. Pat. No. 2,648,775, the two beams are modulated by an interrupter to separately and alternately project the two beams at a rapid frequency into a condenser microphone type detector responsive to the intensity of the beams in the spectral region of interest. The concentration of the fluid to be determined is indicated by the magnitude of the signal difference resulting from the two beams. Although the purpose of the high-frequency alternation was to avoid temperature effects between successive cycles, the instrument had no provision for correcting errors resulting from slower changes in ambient conditions and other instrument instabilities.

SUMMARY OF THE INVENTION

The primary purpose of this invention is to provide a double beam infrared analyzer of enhanced stability. A further object is to provide such an analyzer in which the peak signal derived from the comparison beam is automatically maintained at a predetermined level and in which the comparison beam signal and sample beam signal are equally amplified. Other objects will be apparent from the following description and claims.

The invention is an improvement to infrared analyzers of the type in which the infrared radiation travels along two beam paths, one a sample beam path traversing a gas sample to be analyzed, the other a reference beam traversing a reference gas sample, wherein the presence of the component to be determined in the gas sample, affects the relative intensity of the beams in a spectral region, and wherein the two beams are cyclically modulated by an interrupter to be separately and alternately received by a detector of the condenser microphone type responsive to changes in beam intensity in the said spectral region. The detector generates a series of pulsed signals and the magnitude of alternate pulsed signals indicate the intensity of the detected sample beam and reference beam respectively.

The peak comparison signal is segregated and maintained at a constant value through a feed-back circuit, correcting the comparison signal for analyzer instabilities, and the feed-back circuit controls the degree of amplification of both the comparison signal and the sample signal. Thus the comparison and sample signals are corrected every cycle for instabilities.

BRIEF DESCRIPTION OF THE DRAWINGS

FIG. 1 is a partial diagrammatic illustration of embodiment of this invention showing the interruptor in relation to the infrared beam.

FIG. 2 is a partial diagram of the analyzer of FIG. 1, showing the interruptor in relation to a timing pulse generator.

DESCRIPTION OF THE PREFERRED EMBODIMENT

Figure 3:
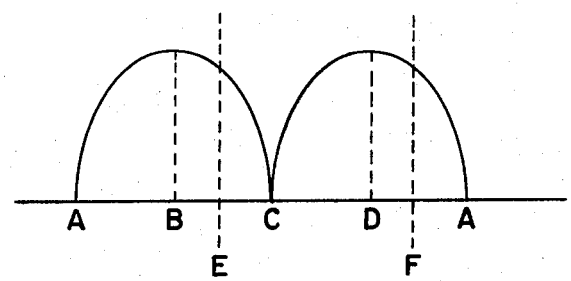
FIG. 3 is a diagram of the signal waveform generated by the analyzer detector.

The presently preferred embodiment is described with reference to FIG. 1, FIG. 2, FIG. 3 and FIG. 4. Infrared sources 2 and 4, for the sample beam and comparison beam respectively, are intersected by a 90° segment, pie-shaped interruptor 6, opaque at least in the spectral region of interest, rotated at a speed of about 2 cps by synchronous motor 8. Each beam is provided with conventional trimmer screw 10 to adjust the intensity of the beam. The sample beam passes through a sample cell 12, which is provided with a sample inlet 14 and outlet 16 and is otherwise sealed by windows 18, transparent to infra-red radiation. The sample beam then enters the chamber 20 of pneumatic detector 22. The comparison beam follows a parallel path through the interruptor region and comparison cell 24, similar to the sample cell except that it contains a fixed volume of reference gas, usually like the sample gas but without the component that is to be measured. The comparison beam then enters chamber 26 of the detector.

The chambers 20 and 26 and the interconnecting passage, delineated by diaphragm 28 of a condenser microphone are filled with a gas which absorb radiation in the same spectral region as the gas being measured, usually the same gas. The gas warms and expands as radiation is absorbed causing the diaphragm to move. The movement of the diaphragm in relation to plate 30 generates a capacitance output signal.

In operation, the interruptor 6 modulates both beams to produce a signal from the pneumatic detector having the wave form showing in FIG. 3. When the interruptor is in the position shown in position A of FIG. 4, with neither beam interrupted, the signal is a null signal shown at point A of FIG. 3. At position B of FIG. 4 the interruptor completely interrupts the comparison beam, giving the peak signal from the sample beam at point B of FIG. 3. In position C of FIG. 4, the output signal is again at a null balance shown at point C of FIG. 3. With the interruptor in position D of FIG. 4, blocking the sample beam, the peak comparison beam signal is obtained at point D of FIG. 3. This type of interruption, which in effect permits the analyzer to function alternately as a single beam sample analyzer and a single beam reference analyzer, was used by Freilino U.S. Pat. No. 3,731,092 for the purpose of obtaining increased detector sensitivity using a flow responsive detector. Equivalent results may be obtained with other interruptors, e.g. an opaque disc having a transparent pie-shaped segment, or reciprocating shutters, it being required only that there be identifiable cycle positions in which the sample beam is entirely suppressed, in which the comparison beam is entirely suppressed and that these cycle portions are non-consecutive and are separated by an intervening cycle portion in which both beams are modulated the same way, thereby generating alternating pulse signals indicating the intensity of the reference beam and sample beams, providing positions in the wave form equivalent to A, B, C. and D of FIG. 3.

With further reference to FIGS. 1 and 2, which schematically illustrate the main elements of the signal treating portion of the analyzer incorporated in conventional supporting circuitry, the capacitance output signal from the detector is amplified and converted to a voltage signal by preamplifier-transducer 34, which voltage signal amplitude is adjusted by attentuator 36, and amplified by operational amplifier 38.

Figure 4:
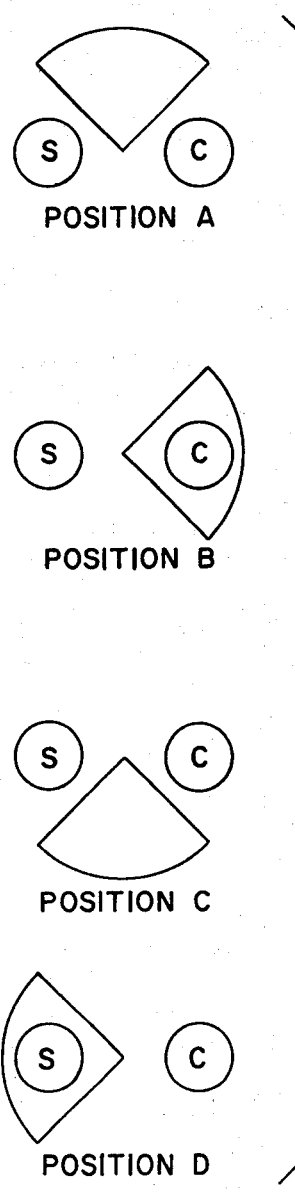
FIG. 4 is a diagram of cyclical interruption positions coordinated with FIG. 2.

The peak detector comprises a diode 40, preventing back current flow, a capacitor 42 in which the peak voltage is stored and three normally open switches, 44, 46 and 48, synchronized by electronic timers 50, 52 and 54 with the interruptor 6. The switches are preferably optical couplers which close momentarily on receiving a timer pulse. The timers are clocked by the 50–60 Hz line supply that also supplies the synchronous motor driving the interruptor, and are reset by a pulse via lead 55 from phototransistor 56, generated when the phototransistor is blocked from LED 58 by the interruptor when the interruptor is in the position A (FIG. 4).

The reset pulse momentarily closes switch 44, discharging capacitor 42, and resets the timers 50, 52 and 54. Switch 44 reopens and, as the interrupter rotates, generating the signal waveform shown in FIG. 2, the peak sample signal at point B is stored on capacitor 42. At a time just following the peak, point E, Timer 52 produces a pulse momentarily closing switch 46, transferring the peak signal from high impedance amplifier 45 to operational amplifier 60 and capacitor 61, serving as a sample peak signal memory. At point C, timer 52 generates a pulse momentarily closing switch 44 to again discharge capacitor 42. The capacitor then stores the peak comparison signal and, at a time following the peak (point F), the timer 54 generates a pulse momentarily closing switch 48, transferring the peak comparison signal for storage by operational amplifier 62 and capacitor 63 serving as a comparison memory.

The output of operational amplifier 62 is connected as the input to feedback amplifier 64, which is referenced against a voltage 66. The output of the feed back amplifier is connected to control attentuator 36, which preferably includes an optical coupler operating in a linear mode to adjust the attentuator proportionally to the output of the feedback amplifier.

The output of sample memory 60 and comparison memory 62 are connected to differential amplifier 68, the output of which is connected to a readout meter 70. The meter indicates the difference in signal amplitude of the sample and comparison memories. This difference is proportional to the sample concentration in the sample cell.

The purpose of the feedback network is to correct for changes within the system by maintaining the comparison signal at a constant value. If the comparison signal does vary and the signal is less than the reference voltage, the feedback amplifier controls the attentuator to increase the amplitude of the signal. Likewise, if the comparison signal is larger than the reference voltage, the feedback amplifier controls the attentuator to decrease the amplitude of the incoming signal. The attentuator controls the amplification of both the comparison and sample signals, so both signals are equally amplified. By performing this level correction in signal, changes in signal level due to instabilities in the infrared detector, preamplifier or amplifier are corrected and the stability of the analyzer is enhanced.

We claim:

1. An infrared analyzer of the type in which the radiation travels along two beam paths, one a sample beam path traversing a gas sample to be analyzed, the other a comparison beam path traversing a reference gas sample, wherein the presence of the component to be determined in the gas sample affects the relative intensity of the beams in a spectral region, the analyzer comprising a detector of the condenser microphone type responsive to changes in the beam intensity in the spectral region, means to cyclically modulate both beams such that in one portion of each cycle the sample beam is interrupted while the reference beam is not interrupted and in another but non-consecutive portion of each cycle the reference beam is interrupted while the sample beam is not, the non-consecutive cycle portions being separated by an intervening cycle portion in which both beams are simultaneously interrupted or simultaneously not interrupted, whereby the detector generates a series of alternate pulsed signals indicating the intensity of the reference beam and sample beam respectively, means to amplify the pulsed signals, means to store the peak value of the amplified comparison signal, feedback means responsive to the amplified comparison signal and controlling the magnitude of amplification to provide a predetermined peak amplitude of the comparison signal, and means to measure the difference between the peak comparison and the peak sample signal.

2. An analyzer according to claim 1 in which the cyclically modulating means comprises a rotating interruptor having a section of about 90° opaque to the spectral region of interest.

3. An analyzer according to claim 1 having a peak detection circuit comprising a capacitor to store peak signals and a first switching means synchronized with the cyclically modulating means to discharge the capacitor during each intervening cycle portion.

4. An analyzer according to claim 3 having a second switching means synchronized with the cyclically modulating means to momentarily connect the capacitor to a first signal storage means after the peak sample signal is stored in the capacitor and before it is discharged, and having a third switching means synchronized with the cyclically modulating means to momentarily connect the capacitor to a second signal storage means after the peak comparison signal is stored in the capacitor and before it is discharged by the first switching means.

5. An analyzer according to claim 4 comprising a feedback amplifier having a reference voltage input and a voltage input from said second signal storage means, the output of the feedback amplifier being proportional to the difference between the voltage input, an optical coupler attentuator connected to attentuate the sample signal and comparison signal, the output of the feedback amplifier connected to the attentuator to adjust the attenuation inversely proportionately to the feedback amplifier output.

6. An analyzer according to claim 3 having a synchronous motor and an electronic timer to produce an electronic pulse at a predetermined time after reset connected to a common alternating current power source, a rotating interruptor driven by the synchronous motor, a timer reset means activated by a predetermined angular position of the interruptor, and an optical coupler switch momentarily closing in response to the timer pulse.

7. An apparatus according to claim 4 comprising a first, second and third timer, each generating an electronic pulse at a different predetermined time after reset; a rotating interruptor; timer reset means activated by a predetermined angular position of the interruptor; a first, second and third optical coupler switch momentarily closing in response to the first, second and third timer pulse respectively.

* * * * *